United States Patent [19]
Zeikus et al.

[11] Patent Number: 5,656,497
[45] Date of Patent: Aug. 12, 1997

[54] GENE ENCODING HYPERTHERMOSTABLE XYLOSE ISOMERASE FROM *THERMOTOGA NEAPOLITANA*

[75] Inventors: Joseph Gregory Zeikus, Okemos; Claire Vieille, East Lansing, both of Mich.

[73] Assignee: Michigan State University, East Lansing, Mich.

[21] Appl. No.: 559,260

[22] Filed: Nov. 15, 1995

Related U.S. Application Data

[62] Division of Ser. No. 302,131, Sep. 6, 1994, abandoned.

[51] Int. Cl.[6] ............................ C12N 9/92; C12N 15/61
[52] U.S. Cl. ..................... 435/320.1; 536/23.2; 435/234
[58] Field of Search ...................... 536/23.2; 435/320.1, 435/234

[56] References Cited

U.S. PATENT DOCUMENTS 5,219,751  6/1993  Starnes et al. ........................... 435/233
5,268,280  12/1993  Starnes et al. ............................ 435/94

OTHER PUBLICATIONS

Brown, S. H., Sjøholm, C. and Kelly, R. M. (1993) Purification and characterization of a highly thermostable glucose isomerase produced by the extremely thermophilic eubacterium, *Thermotoga maritima*. Biotech. Bioeng. 41:878–886.

Lao, D. and Dennis, P. P. (1992) The organization and expression of essential transcription translation components genes in the extremely thermophilic eubacterium *Thermotoga maritima*. JBC 267:22787–22797.

*Primary Examiner*—Keith D. Hendricks
*Attorney, Agent, or Firm*—Quarles & Brady

[57] ABSTRACT

The present invention describes the cloning and expression of a hyperthermostable xylose isomerase gene in an industrial host and the heat facilitated purification of the enzyme. The hyperthermostable enzyme has unique features sought by the fructose syrup industry.

3 Claims, 7 Drawing Sheets

```
      SalI      '         '         '         '         '       60
      GTCGACGCAAAGGTCGTGACGGGTGGAAACATAAACGTTCAGCTGGGAACTGTGTCCTCG

'         '         '         '         '      120
      GCTGCTGTTGAAGGAACATACGTTATCGAAGTTGGACAATTCTCTGGAACGGTCACATCC

'         '         '         '         '      180
      GAGCTTGATGTCAAGATCCGCCGTTGTCCTCAGCACCCCTTCCGTACACCCTGTCATCCT

'    BamHI '         '         '         '      240
      TCACAACGGGGATGAAGGGATCCGTTTCCCACAGCGAAAGATCCCCTGGTGGAACGGTGT

'         '         '         '         '      300
      CTATGTGTGTCACTATCCACAATGTTTTGCTTCTGTCCCTGCCGGGAATGATTGCAAGCA

'         '         '         '         '      360
      GATTCGACCTCCAAATTCCGTTCTGGTCTTTTGTGTCATGACGCTCAACAGTGTATCCCA

'         '         '         '         '      420
      TCTTTTTGAGAAGTTCCTCCAGCCAGTCGGCCTTCTCTTTCTCTCCAGGTCCACCGAAGA

'         '         '         '         '      480
      CTGGATTCACCGAATTGATCGATATGAACCTTTTCAGCGAATCTACCATTTCGTCTTTCA

'         '         '         '         '      540
      ATTCTTCTATCTTTCTTGTTATCTCCATCTGAAACACCTCCCAAGTACAAGTATATCTCT

'         '         '         '         '      600
      CCAAAAAAATATTTGAAATGACCCCAGGGAATTTTATATAATTGATTGATAGAAAAAATT
                   -35                           -10
                '    EcoRI  '         '         '         '      660
      TAGGGAGGTGTTCACATGGCTGAATTCTTTCCAGAAATCCCGAAAGTGCAGTTCGAAGGC
      RBS         MetAlaGluPhePheProGluIleProLysValGlnPheGluGly

'         '         '         '         '      720
      AAAGAAAGCACAAATCCACTTGCGTTCAAGTTCTACGATCCAGAAGAGATCATCGACGGC
      LysGluSerThrAsnProLeuAlaPheLysPheTyrAspProGluGluIleIleAspGly

'         '         '         '         '      780
      AAACCCCTCAAGGACCATCTGAAGTTCTCCGTTGCCTTCTGGCACACCTTCGTGAACGAG
      LysProLeuLysAspHisLeuLysPheSerValAlaPheTrpHisThrPheValAsnGlu

BamHI     '         '         '         '         '      840
      GGAAGGGATCCCTTCGGAGACCCAACGGCCGATCGTCCCTGGAACAGGTACACCGATCCC
      GlyArgAspProPheGlyAspProThrAlaAspArgProTrpAsnArgTyrThrAspPro

'         '         '    EcoR  '         '      900
      ATGGACAAGGCTTTTGCAAGGGTGGACGCCCTTTTTGAATTCTGCGAAAAACTCAACATC
      MetAspLysAlaPheAlaArgValAspAlaLeuPheGluPheCysGluLysLeuAsnIle

'         '         '         '         '      960
      GAGTACTTCTGCTTCCACGACAGAGACATCGCTCCCGAGGGAAAAACGCTGAGGGAGACA
      GluTyrPheCysPheHisAspArgAspIleAlaProGluGlyLysThrLeuArgGluThr
```

FIG. 2B

```
                                                          1020
AACAAAATTTTGGACAAAGTAGTGGAGAGAATCAAAGAGAGAATGAAAGACAGCAACGTG
AsnLysIleLeuAspLysValValGluArgIleLysGluArgMetLysAspSerAsnVal

1080
AAGCTCCTCTGGGGTACTGCAAACCTCTTTTCCCACCCAAGGTACATGCATGGTGCAGCG
LysLeuLeuTrpGlyThrAlaAsnLeuPheSerHisProArgTyrMetHisGlyAlaAla

PstI'                                                1140
ACAACCTGCAGTGCTGATGTTTTTGCGTACGCGGCCGCCCAGGTGAAAAAAGCCCTTGAG
ThrThrCysSerAlaAspValPheAlaTyrAlaAlaAlaGlnValLysLysAlaLeuGlu

1200
ATCACCAAAGAACTTGGAGGAGAAGGGTACGTCTTCTGGGGTGGAAGAGAAGGATACGAA
IleThrLysGluLeuGlyGlyGluGlyTyrValPheTrpGlyGlyArgGluGlyTyrGlu

1260
ACACTCCTCAACACGGACCTTGGATTCGAACTTGAAAACCTCGCCCGCTTCCTCAGAATG
ThrLeuLeuAsnThrAspLeuGlyPheGluLeuGluAsnLeuAlaArgPheLeuArgMet

1320
GCTGTGGATTATGCAAAAAGGATCGGTTTCACCGGACAGTTCCTCATCGAACCAAAACCG
AlaValAspTyrAlaLysArgIleGlyPheThrGlyGlnPheLeuIleGluProLysPro

1380
AAAGAACCCACCAAACACCAGTACGACTTCGACGTTGCAACCGCCTATGCCTTCCTGAAG
LysGluProThrLysHisGlnTyrAspPheAspValAlaThrAlaTyrAlaPheLeuLys

1440
AGCCACGGTCTCGATGAATACTTCAAATTCAACATCGAGGCAAACCACGCCACACTCGCC
SerHisGlyLeuAspGluTyrPheLysPheAsnIleGluAlaAsnHisAlaThrLeuAla

BamHI'                    1500
GGTCACACCTTCCAGCACGAACTGAGAATGGCAAGGATCCTTGGAAAACTCGGAAGCATC
GlyHisThrPheGlnHisGluLeuArgMetAlaArgIleLeuGlyLysLeuGlySerIle

1560
GATGCAAACCAGGGAGACCTTCTTCTTGGATGGGACACCGATCAGTTCCCAACAAACGTC
AspAlaAsnGlnGlyAspLeuLeuLeuGlyTrpAspThrAspGlnPheProThrAsnVal

1620
TACGATACAACCCTTGCAATGTACGAAGTGATAAAAGCGGGAGGCTTCACAAAAGGTGGG
TyrAspThrThrLeuAlaMetTyrGluValIleLysAlaGlyGlyPheThrLysGlyGly

1680
CTCAACTTCGATGCGAAGGTGAGGAGGGCTTCTTACAAAGTGGAGGACCTCTTCATAGGG
LeuAsnPheAspAlaLysValArgArgAlaSerTyrLysValGluAspLeuPheIleGly

1740
CACATAGCGGGAATGGACACCTTTGCACTCGGTTTCAAGGTGGCATACAAACTCGTGAAG
HisIleAlaGlyMetAspThrPheAlaLeuGlyPheLysValAlaTyrLysLeuValLys

1800
GATGGTGTTCTGGACAAATTCATCGAAGAAAAGTACAGAAGTTTCAGGGAGGGCATTGGA
AspGlyValLeuAspLysPheIleGluGluLysTyrArgSerPheArgGluGlyIleGly
```

FIG. 2C

```
                                                                  1860
    AGGGACATCGTCGAAGGTAAAGTGGATTTTGAAAAACTTGAAGAGTATATAATAGACAAA
    ArgAspIleValGluGlyLysValAspPheGluLysLeuGluGluTyrIleIleAspLys

1920
    GAAACGATAGAACTTCCATCTGGAAAGCAAGAATACCTGGAAAGCCTCATCAACAGTTAC
    GluThrIleGluLeuProSerGlyLysGlnGluTyrLeuGluSerLeuIleAsnSerTyr

1980
    ATAGTGAAGACCATTCTGGAACTGAGGTGAAACAGAGTGTGAAGTTCTTGAATCTTCGAA
    IleValLysThrIleLeuGluLeuArg***

2040
    GATTACTTCTTCTGGCACTGATTGCGGCTGGAATCTCAGTGATCATAGTCGTATCCAACC

2100
    GGGAAAACAGGGTGAAATTTCCAGAAGGAGAGATTGTGATAACTGACGGAGAAAGATCTC

2160
    TGAAACTTCGTGTCGAGATAGCGAACACTCCTTTTTTTCGTTCGATCGGTCTGATGTACA

2220
    GAAAGAGCATCCCGGATGACTTCGGGATGCTCTTTGTTTTTGAAGAAGATACAAGAAGCG

2280
    GCTTCTGGATGAAGAACACCTACGTTCCCCTCGAAATCGCCTTCATAGACAGAAACGGCA

2340
    TCGTATTTTCCATTCAGGAGATGGAGCCATGCGAAAAAGAACCCTGCAAGGTTTACTACG

2400
    CACCAAAGCCGTTCAGATACGCTCTTGAAGTGAAAAGAGGTTTTTTCGAAAGGCATGGAT

2460
    TTGGAGTGGGAAGCCGTGTCCTGATAGAAAAGTAGCGGTACTTTCAAACAAAAACGTATG

XbaI
    GAATCTTCATCTTCTTTGCCTCGTACATTCTCGAGTCAGCCATCTTCAGAAGTTCTTCTA
    GA 2522
```

GENE ENCODING HYPERTHERMOSTABLE XYLOSE ISOMERASE FROM *THERMOTOGA NEAPOLITANA*

This is a division of application Ser. No. 08/302,131 filed Sep. 6, 1994, now abandoned.

FIELD OF THE INVENTION

The present invention relates to enzymes. More particularly it relates to enzymes known as xylose isomerases or glucose isomerases.

BACKGROUND OF THE INVENTION

Xylose isomerase (EC 5.3.1.5) is an enzyme that catalyzes the reversible isomerization of D-xylose into D-xylose. It is also called glucose isomerase because of its ability to isomerase D-glucose into D-fructose, and it is therefore widely used in industry for the production of high-fructose corn syrup (HFCS).

The isomerization of glucose reaches an equilibrium which is shifted towards fructose at high temperatures. Presently, the industrial isomerization process is performed at temperatures of about 58° to 60° C., using moderately thermostable xylose isomerases, to produce 40–42% fructose syrup. An additional step of chromatography allows the production of 55% fructose rich HFCS, which has a higher sweetening power than sucrose.

Performing the isomerization at 90° or 95° C. would make possible the production of syrups containing 55% fructose, without the last chromatography step, but the half-life of the enzymes used today at those higher temperatures does not permit increasing the temperature of the isomerization reaction. Another advantage to performing the isomerization at high temperatures would be that it would decrease the risks of microbial contamination of the reactor.

Previous attempts have been made to obtain more thermostable xylose isomerases, either by site-directed mutagenesis of moderately thermostable xylose isomerases, or by screening highly thermophilic organisms for xylose isomerase activity. However, none of those attempts have resulted in commercially useful hyperthermostable xylose isomerases.

It obviously would be advantageous to have a hyperthermostable xylose isomerase and an efficient method of producing that enzyme in quantity.

SUMMARY OF THE INVENTION

It is an object of the present invention to disclose a novel hyperthermostable xylose isomerase.

It is a further object to disclose a method of producing the enzyme employing DNA encoding for the enzyme, plasmids containing the DNA, and bacteria into which the plasmids have been inserted and which produce the enzyme.

It is a still further object to disclose a method of making fructose using the novel hyperthermostable xylose isomerase.

The present invention relates to a hyperthermostable xylose isomerase, which is obtained from the microorganism *Thermotoga neapolitana* (DSM No. 5068) and mutants thereof. The enzyme has the amino acid sequence SEQ ID NO:1 which is:

| 1 | MAEFFPEIPK | VQFEGKESTN | PLAFKFYDPE | EIIDGKPLKD | HLKFSVAFWH |
|---|---|---|---|---|---|
| 51 | TFVNEGRDPF | GDPTADRPWN | RYTDPMDKAF | ARVDALFEFC | EKLNIEYFCF |
| 101 | HDRDIAPEGK | TLRETNKILD | KVVERIKERM | KDSNVKLLWG | TANLFSHPRY |
| 151 | MHGAATTCSA | DVFAYAAAQV | KKALEITKEL | GGEGYVFWGG | REGYETLLNT |
| 201 | DLGFELENLA | RFLRMAVDYA | KRIGFTGQFL | IEPKPKEPTK | HQYDFDVATA |
| 251 | YAFLKSHGLD | EYFKFNIEAN | HATLAGHTFQ | HELRMARILG | KLGSIDANQG |
| 301 | DLLLGWDTDQ | FPINVYDTTL | AMYEVIKAGG | FTKGGLNFDA | KVRRASYKVE |
| 351 | DLFIGHIAGM | DTFALGFKVA | YKLVKDGVLD | KFIEEKYRSF | REGIGRDIVE |
| 401 | GKVDFEKLEE | YIIDKETIEL | PSGKQEYLES | LINSYIVKTI | LELR. |

Thermotoga is a highly thermophilic organism, originating from geothermally heated sea floors, and deeply branched in eubacteria. A hyperthermostable xylose isomerase has been purified from the species *T. maritima* and has been shown to have an optimal activity at 105°–110° C.

The *T. neapolitana* which produces the enzyme of the present invention has an optimum growth temperature of about 77° C. and its growth rate is higher than 50% of the maximum at temperatures from 64° to 87° C. (1). Its optimum growth pH is 7.5, and its growth rate is higher than 50% of the maximum at pHs from 6.0 to 9.0.

The xylose isomerase that is produced by *T. neapolitana* is optimally active at 97° C. and it retains 40% of its activity after incubation at 90° C. for 2 hours in the absence of substrate. It retains 60% of its activity after incubation at 80° C. for 2 hours in the absence of substrate. It retains 55% of its activity after incubation at 70° C. for 4 hours in the absence of substrate and 90% of its activity after incubation at 50° C. for 4 hours in the absence of substrate.

The xylose isomerase retains 100% of its activity at pHs of from 6.8 to 7.3 for at least 30 minutes. It has an optimum pH for activity of 7.1, but also shows:

More than 70% activity between pHs 5.8 and 7.7
More than 80% activity between pHs 6.1 and 7.6
More than 90% activity between pHs 6.6 and 7.4

The xylose isomerase of the present invention has the following additional physiochemical properties:

(1) Reactivity: It isomerizes xylose to produce D-xylulose and D-glucose to produce D-fructose.

(2) Activity: It has a specific activity of greater than 21 U/mg of purified enzyme.

(3) The enzyme is composed of identical subunits of about 50,000 daltons, as measured by SDS polyacrylamide gel electrophoresis.

The preferred method of the present invention for producing the enzyme, comprises, isolating and purifying chromosomal DNA from *T. neapolitana* strain 5068, partially digesting the chromosomal DNA with a restriction enzyme, ligating the DNA into a plasmid vector, transforming the *E. coli* with the ligation mixture, growing the *E. coli* and isolating the enzyme from the E. coli. The enzyme can then be purified by heating it to about 90° C. for about 150 minutes. Most E. coli proteins are denatured during this treatment and the last E. coli proteins can be eliminated by chromatographic steps to obtain the purified xylose isomerase.

The novel isolated hyperthermostable xylose isomerase gene has the nucleotide sequence of SEQ ID NO:2. The nucleotide sequence SEQ ID NO:2 is:

BRIEF DESCRIPTION OF DRAWINGS

FIG. 1: Physical and genetic maps of pTNE1 and construction of the plasmids used in this study. Restriction sites: B, BamHI; H, HindIII; P, PstI; R, EcoRI; S, SalI; X, XbaI. Plasmid vectors are not shown. ΔSal originated from pTNE1 by the deletion of a SalI fragment, using the unique SalI site

| 1 | GTCGACGCAA | AGGTCGTGAC | GGGTGGAAAC | ATAAACGTTC | AGCTGGGAAC |
|---|---|---|---|---|---|
| 51 | TGTGTCCTCG | GCTGCTGTTG | AAGGAACATA | CGTTATCGAA | GTTGGACAAT |
| 101 | TCTCTGGAAC | GGTCACATCC | GAGCTTGATG | TCAAGATCCG | CCGTTGTCCT |
| 151 | CAGCACCCCT | TCCGTACACC | CTGTCATCCT | TCACAACGGG | GATGAAGGGA |
| 201 | TCCGTTTCCC | ACAGCGAAAG | ATCCCCTGGT | GGAACGGTGT | CTATGTGTGT |
| 251 | CACTATCCAC | AATGTTTTGC | TTCTGTCCCT | GCCGGGAATG | ATTGCAAGCA |
| 301 | GATTCGACCT | CCAAATTCCG | TTCTGGTCTT | TTGTGTCATG | ACGCTCAACA |
| 351 | GTGTATCCCA | TCTTTTTGAG | AAGTTCCTCC | AGCCAGTCGG | CCTTCTCTTT |
| 401 | CTCTCCAGGT | CCACCGAAGA | CTGGATTCAC | CGAATTGATC | GATATGAACC |
| 451 | TTTTCAGCGA | ATCTACCATT | TCGTCTTTCA | ATTCTTCTAT | CTTTCTTGTT |
| 501 | ATCTCCATCT | GAAACACCTC | CCAAGTACAA | GTATATCTCT | CCAAAAAAAT |
| 551 | ATTTGAAATG | ACCCCAGGGA | ATTTTATATA | ATTGATTGAT | AGAAAAAATT |
| 601 | TAGGGAGGTG | TTCACATGGC | TGAATTCTTT | CCAGAAATCC | CGAAAGTGCA |
| 651 | GTTCGAAGGC | AAAGAAAGCA | CAAATCCACT | TGCGTTCAAG | TTCTACGATC |
| 701 | CAGAAGAGAT | CATCGACGGC | AAACCCCTCA | AGGACCATCT | GAAGTTCTCC |
| 751 | GTTGCCTTCT | GGCACACCTT | CGTGAACGAG | GGAAGGGATC | CCTTCGGAGA |
| 801 | CCCAACGGCC | GATCGTCCCT | GGAACAGGTA | CACCGATCCC | ATGGACAAGG |
| 851 | CTTTTGCAAG | GGTGGACGCC | CTTTTTGAAT | TCTGCGAAAA | ACTCAACATC |
| 901 | GAGTACTTCT | GCTTCCACGA | CAGAGACATC | GCTCCCGAGG | GAAAAACGCT |
| 951 | GAGGGAGACA | AACAAAATTT | TGGACAAAGT | AGTGGAGAGA | ATCAAAGAGA |
| 1001 | GAATGAAAGA | CAGCAACGTG | AAGCTCCTCT | GGGGTACTGC | AAACCTCTTT |
| 1051 | TCCCACCCAA | GGTACATGCA | TGGTGCAGCG | ACAACCTGCA | GTGCTGATGT |
| 1101 | TTTTGCGTAC | GCGGCCGCCC | AGGTGAAAAA | AGCCCTTGAG | ATCACCAAAG |
| 1151 | AACTTGGAGG | AGAAGGGTAC | GTCTTCTGGG | GTGGAAGAGA | AGGATACGAA |
| 1201 | ACACTCCTCA | ACACGGACCT | TGGATTCGAA | CTTGAAAACC | TCGCCCGCTT |
| 1251 | CCTCAGAATG | GCTGTGGATT | ATGCAAAAAG | GATCGGTTTC | ACCGGACAGT |
| 1301 | TCCTCATCGA | ACCAAAACCG | AAAGAACCCA | CCAAACACCA | GTACGACTTC |
| 1351 | GACGTTGCAA | CCGCCTATGC | CTTCCTGAAG | AGCCACGGTC | TCGATGAATA |
| 1401 | CTTCAAATTC | AACATCGAGG | CAAACCACGC | CACACTCGCC | GGTCACACCT |
| 1451 | TCCAGCACGA | ACTGAGAATG | GCAAGGATCC | TTGGAAAACT | CGGAAGCATC |
| 1501 | GATGCAAACC | AGGGAGACCT | TCTTCTTGGA | TGGGACACCG | ATCAGTTCCC |
| 1551 | AACAAACGTC | TACGATACAA | CCCTTGCAAT | GTACGAAGTG | ATAAAAGCGG |
| 1601 | GAGGCTTCAC | AAAAGGTGGG | CTCAACTTCG | ATGCGAAGGT | GAGGAGGGCT |
| 1651 | TCTTACAAAG | TGGAGGACCT | CTTCATAGGG | CACATAGCGG | GAATGGACAC |
| 1701 | CTTTGCACTC | GGTTTCAAGG | TGGCATACAA | ACTCGTGAAG | GATGGTGTTC |
| 1751 | TGGACAAATT | CATCGAAGAA | AAGTACAGAA | GTTTCAGGGA | GGGCATTGGA |
| 1801 | AGGGACATCG | TCGAAGGTAA | AGTGGATTTT | GAAAAACTTG | AAGAGTATAT |
| 1851 | AATAGACAAA | GAAACGATAG | AACTTCCATC | TGGAAAGCAA | GAATACCTGG |
| 1901 | AAAGCCTCAT | CAACAGTTAC | ATAGTGAAGA | CCATTCTGGA | ACTGAGGTGA |
| 1951 | AACAGAGTGT | GAAGTTCTTG | AATCTTCGAA | GATTACTTCT | TCTGGCACTG |
| 2001 | ATTGCGGCTG | GAATCTCAGT | GATCATAGTC | GTATCCAACC | GGGAAAACAG |
| 2051 | GGTGAAATTT | CCAGAAGGAG | AGATTGTGAT | AACTGACGGA | GAAAGATCTC |
| 2101 | TGAAACTTCG | TGTCGAGATA | GCGAACACTC | CTTTTTTTCG | TTCGATCGGT |
| 2151 | CTGATGTACA | GAAAGAGCAT | CCCGGATGAC | TTCGGGATGC | TCTTTGTTTT |
| 2201 | GAAGAAGAT | ACAAGAAGCG | GCTTCTGGAT | GAAGAACACC | TACGTTCCCC |
| 2251 | TCGAAATCGC | CTTCATAGAC | AGAAACGGCA | TCGTATTTTC | CATTCAGGAG |
| 2301 | ATGGAGCCAT | GCGAAAAAGA | ACCCTGCAAG | GTTTACTACG | CACCAAAGCC |
| 2351 | GTTCAGATAC | GCTCTTGAAG | TGAAAAGAGG | TTTTTTCGAA | AGGCATGGAT |
| 2401 | TTGGAGTGGG | AAGCCGTGTC | CTGATAGAAA | AGTAGCGGTA | CTTTCAAACA |
| 2451 | AAAACGTATG | GAATCTTCAT | CTTCTTTGCC | TCGTACATTC | TCGAGTCAGC |
| 2501 | CATCTTCAGA | AGTTCTTCTA | GA. | | |

The novel recombinant plasmid comprises a compatible vector containing the DNA sequence of SEQ ID NO:2. A compatible vector is one into which the gene can be inserted and which can be introduced into a suitable host for production of the enzyme.

The preferred method of preparing D-fructose comprises enzymatically treating D-glucose with the hyperthermostable xylose isomerase of the present invention at a temperature of about 80° C. to about 100° C. at a pH of about 5.8 to 7.7 to obtain a syrup containing up to about 55% D-fructose.

The achievement of the above and other objects and advantages of the present invention will be apparent to those skilled in the art from the description of the drawings, the preferred embodiment and the experimental work.

from pUC18. pTNE2 and 3 contain a 2.5 kb SalI-XbaI fragment from pTNE1 cloned in pBluescriptKS+ and KS- respectively. R3 and R9 contain the 2 kb EcoRI fragment from pTNE1 cloned in pBluescript in opposite orientations. The hatched box represents the smallest fragment of pTNE1 hybridizing with the probe used for the library screening. The location and transcriptional direction of the xylA gene are indicated by the arrow.

DESCRIPTION OF PREFERRED EMBODIMENT

The hyperthermostable enzyme from *Thermotoga neapolitana* strain 5068 (DSM No. 5068.) is more stable at high temperatures (90° C.) than the enzymes from conventional or moderate thermophilic organisms. During the production of high-fructose corn syrup, the use of a highly thermostable xylose isomerase in the glucose isomerization process allows the reaction to proceed at higher temperatures, so that syrups with a higher fructose content can be obtained due to chemical equilibrium.

The preferred method of producing the enzyme broadly comprises expressing an active and thermostable enzyme in a mesophilic organism which allows the addition of a heat treatment step, which improves dramatically the purification procedure.

In an especially preferred practice of the method of the invention chromosomal DNA from *T. neapolitana* strain 5068 is purified by the method of Goldberg and Ohman (2). The chromosomal DNA is partially digested with the restriction enzyme Sau3AI. The 3–7 kb fragments are isolated from a sucrose gradient (10–40%), and ligated into plasmid vector pUC18, which is cut by BamHI and dephosphorylated with calf intestine alkaline phosphatase to form a hybrid plasmid. *E. Coli* SURE strain is transformed with the ligation mixture, and recombinants which contain the xylose isomerase gene are selected by colony hybridization using a PCR-generated homologous probe (3). Lastly, positive clones are tested for xylose isomerase activity at 90° C.

A further understanding of the invention can be obtained from the following description of the experimental work we performed.

EXPERIMENTAL

MATERIALS AND METHODS

Bacterial strains and plasmids.

Figure 1:
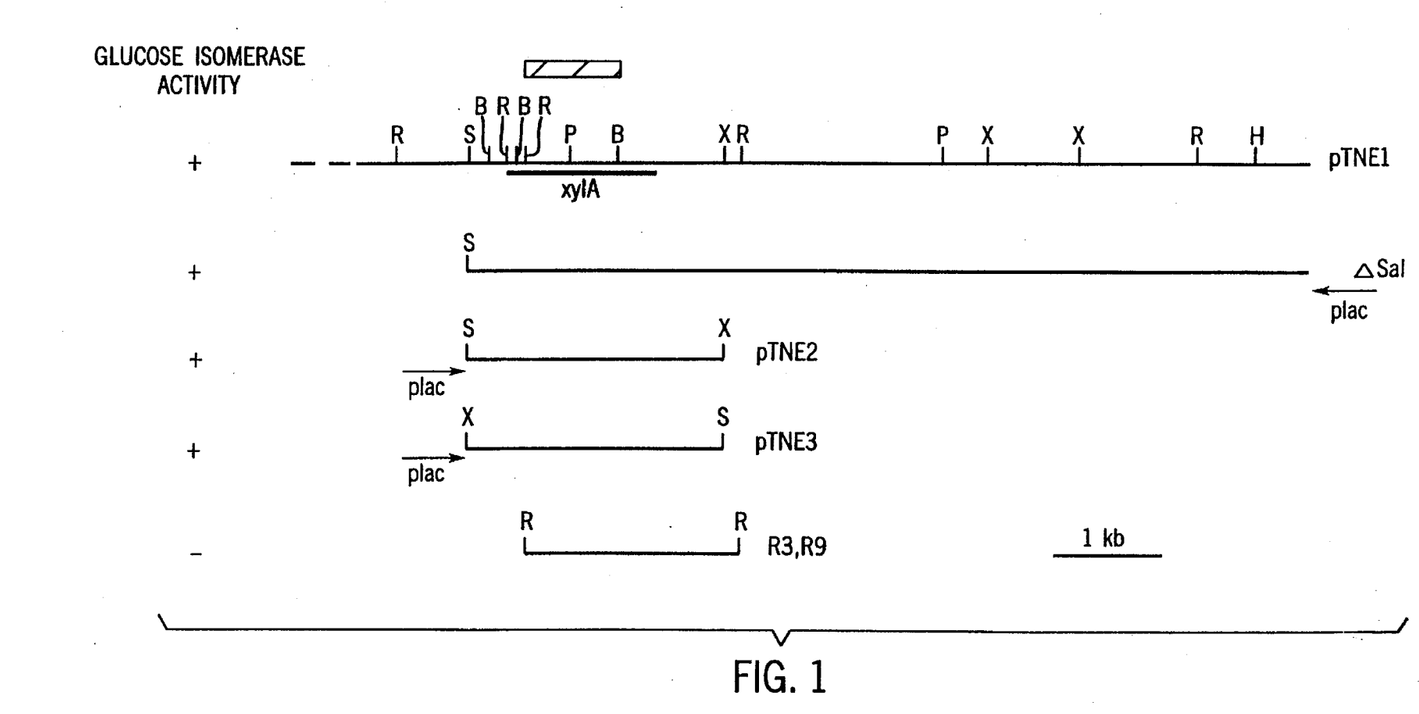
Figure 2A:
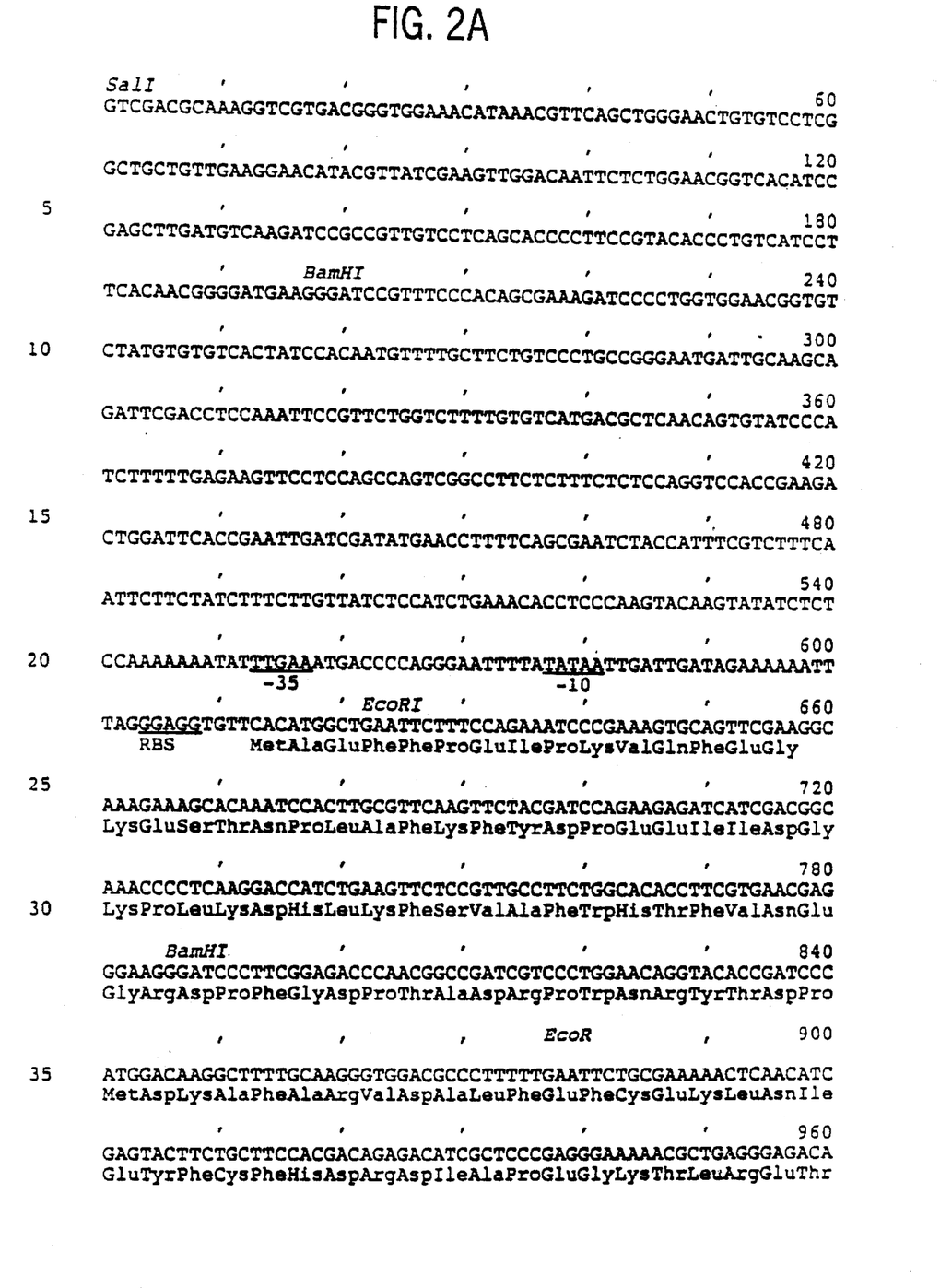
FIG. 2: Nucleotide sequence and deduced amino acid sequence of the T. neapolitana 5068 xylose isomerase gene. The putative −35 and −10 sequences in the promoter region and the putative ribosome binding site (RBS) are underlined. A terminator-like, inverted repeat sequence is indicated by horizontal arrows. The restriction sites used in this study are shown above the nucleotide sequence.
Figure 2C:
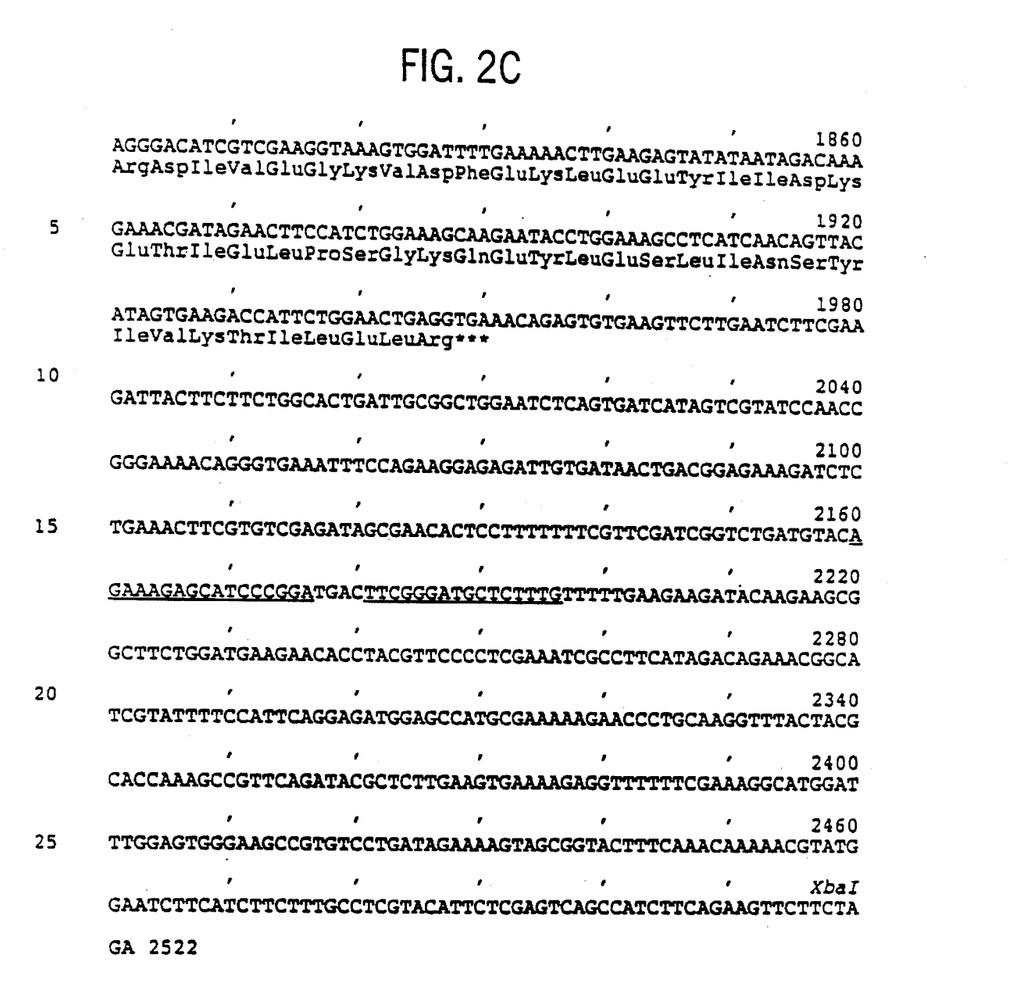
Figure 3:
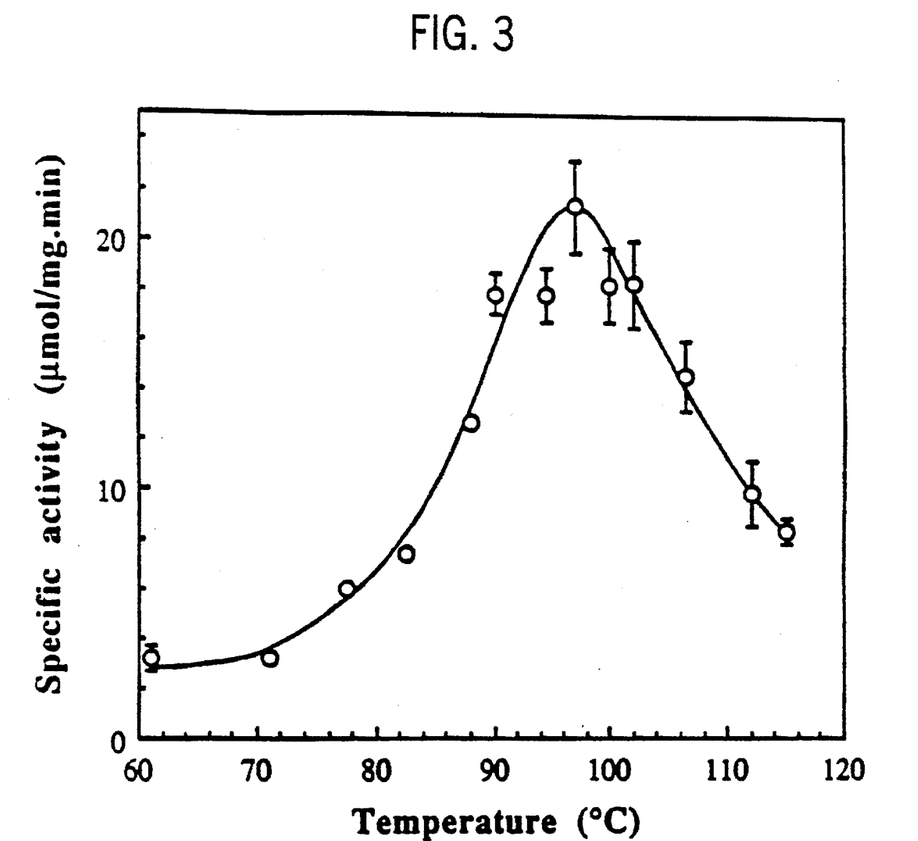
FIG. 3: Effect of temperature on the glucose isomerase specific activity of T. neapolitana xylose isomerase. Values are the mean of 2 or 3 independent assays.
Figure 4A:
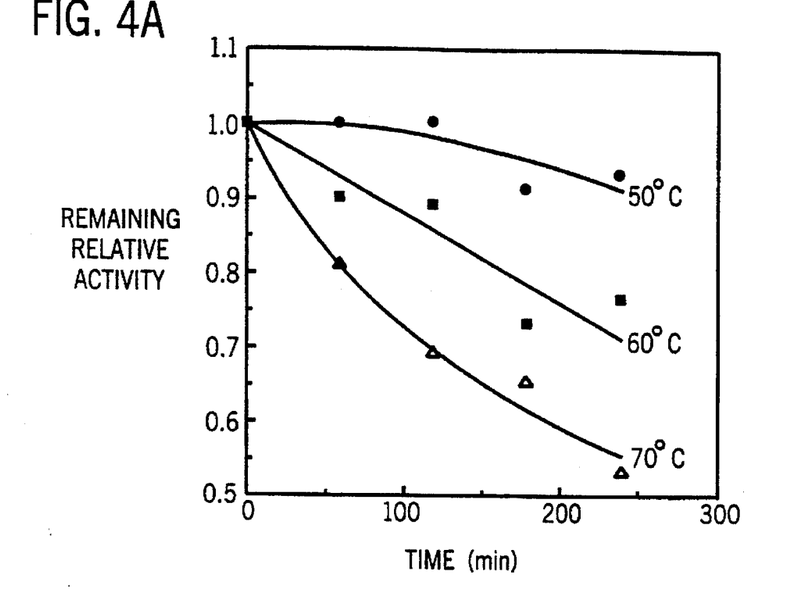
FIG. 4(a) and (b): Time course of irreversible thermoinactivation of T. neapolitana xylose isomerase. Values are the mean of 3 independent assays.
Figure 4B:
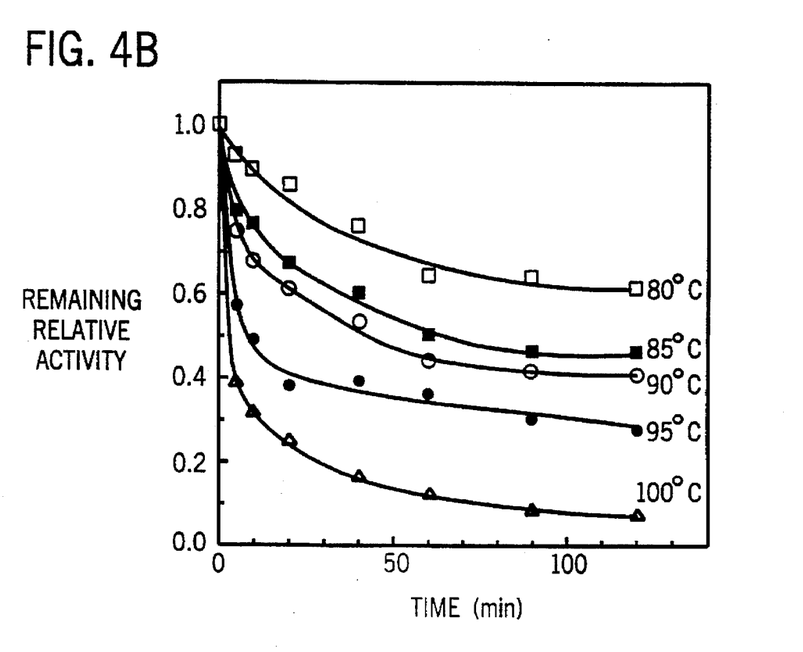
Figure 5:
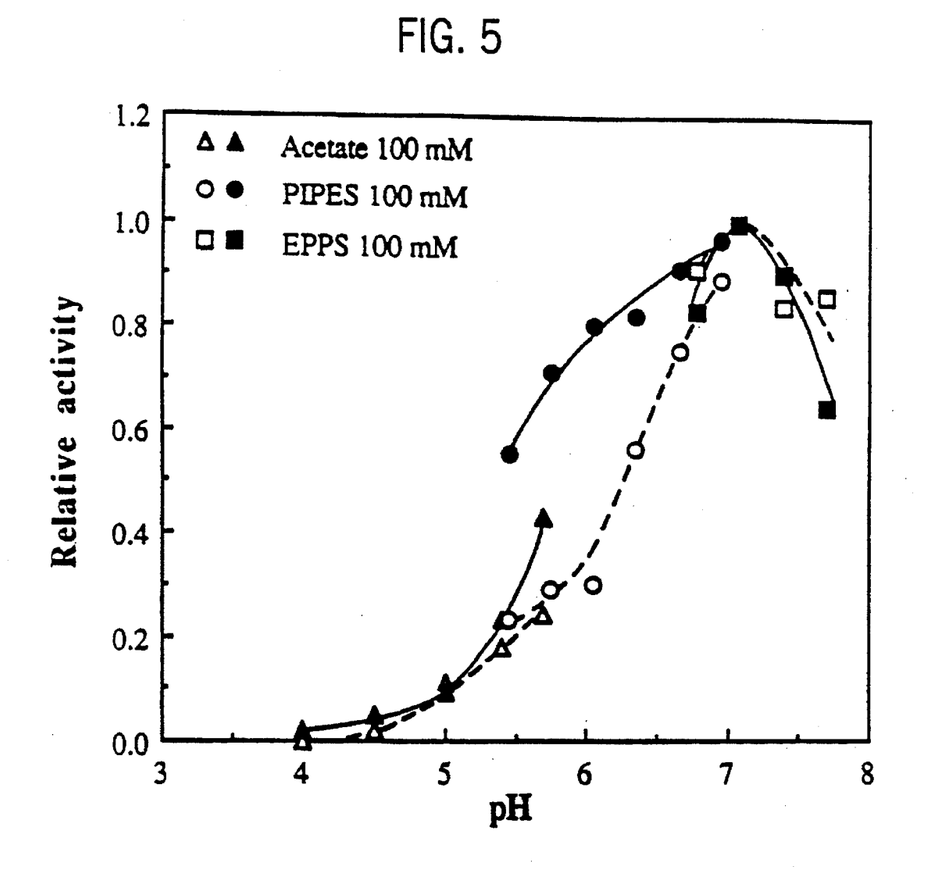
FIG. 5: Effect of pH on the specific activity and stability of T. neapolitana xylose isomerase. Closed symbols are relative activities measured at 90° C. Open symbols are residual relative activities, as measured at pH 7.0, after incubation for 30 min at 90° C. Values are the mean of 3 independent assays. Standard deviations ($\sigma_{n-1}$) are shown, deviations increase at high temperatures, where non-enzymic isomerization becomes significant.

*Thermotoga neapolitana* strain 5068 was used as a source of chromosomal DNA to construct the library. *Escherichia coli* Sure strain (e14⁻ (mcrA), Δ(mcrCB-hsdSMR-mrr)171, sbcC, recB, recJ, umuC::Tn5 (kan$^r$), uvrC, supE44, lac, gyrA96, relA1, thi-1, endA1, [F′ proAB, lacI$^q$ZΔM15, Tn10, (tet$^r$)]) (Stratagene, La Jolla, Calif.) was used for the cloning experiments, and *E. coli* xyl⁻ mutant HB101 (F⁻, hsdS20, ara-1, recA13, proA12, lacY1, galK2, rpsL20, mtl-1, xyl-5) (4) was used for the purification of the recombinant xylose isomerase. Plasmids pUc18 (Pharmacia, Piscataway, N.J.) and pBluescriptIIKS+ (pBSIIKS+) and (Stratagene, La Jolla, Calif.) were used as cloning vectors. Plasmids constructed in this study are shown in FIG. 1.

Media and growth conditions.

*T. neapolitana* cultures were grown in modified ASW (5) at 80° C. *E. coli* cultures were grown in Luria broth (10 g tryptone, 5 g yeast extract, 5 g NaCl per liter), except for the purification of the recombinant xylose isomerase, where Terrific Broth (TB) was used (6). The antibiotics ampicillin and kanamycin (kan) were used at 100 μg/ml and 25 μg/ml respectively.

DNA preparation and genomic library construction.

Chromosomal DNA from *T. neapolitana* strain 5068 was purified by the method of Goldberg and Ohman (2). The chromosomal DNA was partially digested with the restriction enzyme Sau3AI. The 3–7 kb fragments were isolated from a sucrose gradient (10–40%), and ligated into plasmid vector pUC18, which was cut by BamHI and dephosphorylated with calf intestine alkaline phosphatase. *E. Coli* (SURE strain) was transformed with the ligation mixture by electroporation (3).

Manipulation of DNA.

Plasmid DNA purification, restriction analysis, PCR reaction, and colony and DNA hybridization were performed by conventional techniques (6) (3). The following oligonucleotides (obtained from the Michigan State University Macromolecular Facility) were used for PCR reactions: 5'-CCA AGC TTN ACN CAY CCN GTN TTY AAR GA3' (A, encodes the peptide FTHPVFKD), where the AAGCTT sequence creates a HINDIII site; 5'-GAR CCN AAR CCN AAY GAR CCG CGG-3' (B, encodes the peptide EPKPNEP), where the CCGCGG sequence creates a SacII site; 5'-GGT CTA GAR AAY TAY GTN TTY TGG GGN GG-3' (C, encodes the peptide ENYVFWGG), where the TCTAGA sequence creates an XbaI site. DNA was recovered from agarose gels with the Geneclean II kit (BIO 101, La Jolla, Calif.). Plasmid pTNE2 was stabilized by cloning the kan$^r$ cartridge from pUC-4K (Pharmacia, Piscataway, N.J.) into the pTNE2 unique SalI site, giving rise to plasmid pTNE2::kan.

Nucleotide sequence determination.

Sequential deletions of pTNE2 were created by the exonuclease III digestion procedure of Henikoff (7). Sequences were determined, on both strands, by the dideoxy chain termination technique (8), using the Sequenase Version 2.0 kit (U.S. Biochemical Corp., Cleveland, Ohio). The sequencing data were analyzed using the Sequence Analysis Software Package of the Genetics Computer Group, version 5 (University of Wisconsin) (9). Hydrophobic cluster analysis (HCA) of the amino acid sequences was performed as described by Gaboriaud et al. (10) and Lemesle-Varloot et al. (11) with the HCA plot program, version 2, from Doriane (Le Chesnay, France).

Enzyme purification.

For comparison purposes *Thermoanaerobacterium thermosulfurigenes* 4B recombinant xylose isomerase was purified from *E. coli* HB101 carrying plasmid pCMG11-3, as described by Lee et al. (12), except that: i) 50 mM MOPS (4-morpholinepropanesulfonic acid) (pH7.0) containing 5 mM MgSO$_4$ plus 0.5 mM CoCl$_2$ was used as buffer; ii) a (NH$_4$)$_2$SO$_4$ fractionation step was added after the heat treatment (13); iii) ion exchange chromatography was performed on Q-Sepharose Fast Flow, and proteins were eluted with a linear NaCl gradient (0.0–0.3M).

*T. neapolitana* recombinant xylose isomerase was purified from *E. coli* HB101 carrying plasmid pTNE2::kan as described above, except that: i) the cells were grown in TB supplemented with kan; ii) the cell extract was heat treated at 90° C. for 2 h 30 min in an oil shaking bath.

Protein concentration was determined routinely by the method of Bradford (14), using the Bio-Rad protein reagent.

Bovine serum albumin was used as the standard. Protein concentration of pure enzyme preparations was estimated at 280 nm, on denaturated enzyme. The extinction coefficient (e=52950) was calculated from the sequence, using the Sequence Analysis Software Package of the Genetic Computer Group program. Enzyme fractions were analyzed by SDS-12% polyacrylamide gel electrophoresis, and visualized by Coomassie blue staining.

Enzyme assays.

Cell extracts prepared by sonication and purified preparations were used as enzyme sources. To determine the effect of temperature on glucose isomerase specific activity, glucose isomerase activity was measured by incubating the enzyme (0.02–0.1 mg/ml) in 100 mM MOPS (pH 7.0 at room temperature), 1 mM $CoCl_2$ and 0.8M glucose for 20 min. According to $\Delta pKa/\Delta t$ of MOPS buffer which is –0.011 (US Biochemical, Cleveland, Ohio, catalog 1993, p. 290), the pH was 6.3 at 90° C. The reaction was stopped by cooling the tubes in ice. The fructose was assayed by the cysteine-carbazole/sulfuric acid method (15). One unit of isomerase activity is defined as the amount of enzyme that produced 1 µmole of product/min under the assay conditions.

Thermostability studies.

The enzyme was incubated at different temperatures in the presence of 100 mM MOPS (pH 7.0), 1 mM $CoCl_2$ at room temperature for different periods of time. Thermoinactivation was stopped by cooling the tubes in a water bath equilibrated at room temperature. The residual glucose isomerase activity was measured in the conditions described above.

pH studies.

The effect of pH on glucose isomerase activity was measured using the standard protocol described above for enzyme assays, except that the MOPS buffer was substituted by acetate 100 mM (pH 4.0–5.7), PIPES (piperazine-N,N'-bis-[2-ethanesulfonic acid]) 100 mM (pH 6.0–7.5), or EPPS (N-[2-hydroxyethyl]piperazine-N'-[3-propanesulfonic acid]) 100 mM (pH 7.5–8.7). All pHs were adjusted at room temperature, and the $\Delta pKa/\Delta t$ for acetate, PIPES, and EPPS (0.000, –0.0085, and –0.011 respectively) (16, USB catalog 1993, p. 290) were taken into account for the results (FIG. 6). The effect of pH on enzyme stability was measured by incubating the enzyme (0.5–1.0 mg/ml) at 90° C. for 30 min in acetate 100 mM (pH 4.0–5.7), PIPES 100 mM (pH 6.0–7.5), or EPPS 100 mM (pH 7.5–8.7), in the presence of 0.5 mM $CoCl_2$. The inactivation was stopped by cooling the tubes in a water bath equilibrated at room temperature. The residual glucose isomerase activity was measured at pH 7.0, using the standard protocol. The enzyme was diluted ten-fold in the reaction mixture.

Cloning of the xylose isomerase gene.

The first attempts to clone *T. neapolitana* by complementation of a xyl⁻ strain of *E. coli* were unsuccessful. This result was expected, since no xylose isomerase activity could be detected with the xylose isomerase purified from *T. maritima*, at temperatures compatible with *E. coli* growth (5). On the other hand, no hybridization signal could be detected in *T. neapolitana* genomic DNA with the *Thermoanaerobacterium thermohydrosulfuricum* 4B xylA gene as a probe.

We therefore tried to amplify a DNA fragment, internal to the *T. neapolitana* xylA gene, and use it as a probe to screen a plasmid library. To design primers for PCR, the amino acid sequences of the xylose isomerases from *Actinoplanes missouriensis* (17), *Ampullariella* (18), *Streptomyces rubuginosus* (19), *S. violaceoniger* (20), *Bacillus subtilis* (21), *Lactobacillus brevis* (22), *L. pentosus* (23), *Thermoanaerobacterium thermosulfurigenes* 4B, *Staphylococcus xylosus* (24), and *E. coli* (25) have been aligned (not shown) to identify highly conserved regions. Two main families of highly conserved enzymes were identified, the first included the *Streptomyces, Ampullariella* and *A. missouriensis* and the second included Bacillus, the Lactobacilli, and *T. thermosulfurigenes*. Even if they were more related to family II xylose isomerases, *E. coli* and *S. xylosus* enzymes still stood apart, and were not taken into account in the following. Only the sequence EPKPN/KEP (positions 232 to 238 in *T. thermosulfurigenes* enzyme) was conserved among the proteins of the 2 families. The sequence ENYVFWG (positions 183 to 189 in *T. thermosulfurigenes* enzyme) was conserved only in family II, whereas the sequence FTHPVFKD (positions 94 to 100 in *A. missouriensis* enzyme) was conserved only in family I. Since we did not know to which family the *T. neapolitana* enzyme would belong, we designed two sets of primers to correspond to the 2 families. With primers A plus B we expected a 294 bp PCR product, and with primers C plus B we expected a 180 bp PCR product.

With *T. neapolitana* genomic DNA as the template, only the PCR reaction using primers C plus B gave rise to a single band of the expected size in a reproducible way. This PCR product has been cloned into the XbaI-SacII sites of pBSIIKS+ and sequenced. It encodes a 54 residues polypeptide, 80% identical to the part of *T. thermosulfurigenes* xylose isomerase chosen for the amplification. This PCR fragment was used as a probe to screen a *T. neapolitana* genomic library. Among 15,000 clones that were screened by colony hybridization, only 6 hybridized strongly with the probe, and were completely isolated. Restriction analysis of these clones revealed that they all overlapped. All of them showed xylose isomerase activity.

One of them, clone pTNE1 (FIG. 1), was chosen for further studies. Additional hybridizations with restriction digests of pTNE1 showed that a 750 bp EcoRI-BamHI fragment carried the homology with the PCR probe. Several sub-clones were constructed, and tested for xylose isomerase activity (FIG. 1). Compared to pTNE1, the same level of activity was detected with both pTNE2 and 3. Since the insert was in opposite orientation in pTNE2 and pTNE3, when referring to the lacZ promoter, the xylose isomerase gene carried by the insert is probably expressed from its own promoter. No activity could be detected with R3 and R9.

Nucleotide sequence of the xylose isomerase gene.

The 2.4 kb SalI-XbaI insert of pTNE2 has been sequenced. One open reading frame (ORF) of 1332 nt, encodes a 444 AA polypeptide (calculated molecular weight: 50,892), 70% identical to the 4B xylose isomerase. This ORF is preceded by a Shine-Dalgarno sequence, GGAGGT, which exactly matches the *T. maritima* 16S rRNA sequence 3'-CCUCCA-5' (26). A potential promoter, TTGAA (–35) TATAAT (–10), corresponding to the consensus defined for *T. maritima* (27) is present 63 bp upstream of the ATG start codon. An inverted repeat located 213 pb downstream of xylA might be involved in termination of transcription. No homology was found upstream and downstream of xylA with *E. coli* xylB. The genetic organization of the xylose metabolism genes therefore seems different from what has been described in other microorganisms, where xylA and xylB are usually co-transcribed. The overall G+C content of xylA is 47% (Thermotogales have a genomic G+C content of 40 to 46%). The G+C content in codon position 3 is 59% (it is 60% for *T.maritima* ompα); this content is 15% higher than what is expected in an organism with 46% genomic G+C.

Comparison of the protein sequences.

The *T. neapolitana* xylose isomerase clearly belongs to the xylose isomerase family of type II, including the enzymes from *E. coli, B. subtilis, C. thermohydrosulfuricum,* and *T. thermosulfurigenes* strain 4B. Enzymes of type I are shorter by 40 to 50 residues at the N-terminal. The catalytic triad (His101, Asp104, Asp339), as well as almost all the other residues involved either in substrate or metal binding are conserved among the two protein families.

Biochemical characterization of *T. neapolitana* xylose isomerase.

Since plasmid pTNE2 was unstable in *E. coli* HB101, reliable amounts of *T. neapolitana* xylose isomerase were purified from HB 101(pTNE2::kan) cultures, grown in the presence of kanamycin. Heat treatment of the cell extracts for 2 h 30 min at 90° C. was a highly efficient step. The main contaminating protein was further removed by ammonium sulfate fractionation, and a last step of ion exchange chromatography allowed to purify the protein to homogeneity (not shown). The purified xylose isomerase is a tetramer composed of identical subunits of 50,000 Da.

The cloned xylose isomerase is optimally active at temperatures as high as 94°–100° C.

By the exercise of the method of the present invention a highly thermostable and thermophilic xylose isomerase has been cloned from the hyperthermophile *T. neapolitana* 5068. This enzyme clearly belongs to the xylose isomerase family II. Although 70% identical to the *Thermoanaerobacterium thermosulfurigenes* 4B enzyme and, according to the HCA comparison, showing highly conserved secondary structures, the Thermotoga xylose isomerase is unexpectedly optimally active at temperatures 15° C. higher than the 4B enzyme (95° C. versus 80° C.).

Representative of the plasmids and viral vectors which can be used in the method of the present invention are the following: pUC plasmids and derivatives like pTZ18-19, pBluescript, with high plasmid copy number per cell (200–300); pBR322 and derivatives, with lower copy number (20–50); plasmids with low copy number (5–10) like pMMB67EH (Fürste et al., 1986) (28); and plasmids able to replicate in *B. subtilis* or other food-safe strains.

In general any plasmid can be used in which the gene can be inserted; which is stable when transformed into a bacteria and which will cause the bacteria to express the enzyme in a recoverable form.

Representative of the bacteria which can be employed in addition to the HB101 strain of *E. coli* are the following: other *E. coli* strains (no background glucose isomerase activity originating from *E. coli* can be detected after the heat treatment included in our protocol); *B. subtilis* strains, and other food-safe bacterial strains.

It will be apparent to those skilled in the art that a number of changes and modifications can be made without departing from the spirit and scope of the invention. Therefore, it is intended that the invention only be limited by the claims.

REFERENCES (1) Belkin, S., Wirsen, C. O. and Jannasch, H. W. (1986) A new sulfur-reducing, extremely thermophilic eubacterium from a submarine thermal vent. Appl. Environ. Microbiol. 51:1180–1185.

(2) Goldberg, J. B. and Ohman D. E. (1984) Cloning and expression in *Pseudomonas aeruginosa* of a gene involved in the production of alginate. J. Bacteriol. 158:1115–1121.

(3) Ausubel, F. M., Brent, R., Kingston, R. E., Moore, D. D., Seidman, J. G., Smith, J. A. and Struhl, K. (eds) Current protocols in molecular biology. Greene Publishing & Wiley-Interscience, New York, N.Y.

(4) Boyer, H. W. and Roulland-Dussoix, D. (1969) A complementation analysis of the restriction and modification of DNA in *Escherichia coli.* J. Mol. Biol. 41:459–472.

(5) Brown, S. H., Sjøholm, C. and Kelly, R. M. (1993) Purification and characterization of a highly thermostable glucose isomerase produced by the extremely thermophilic eubacterium, *Thermotoga maritima.* Biotech. Bioeng. 41:878–886.

(6) Sambrook, J., Fritsch, E. and Maniatis, T. (1989) Molecular cloning, 2nd edn, vol 1–3. Cold Spring Harbor Laboratory Press, Cold Spring Harbor, N.Y.

(7) Henikoff, S. (1984) Unidirectional digestion with exonuclease III creates targeted breakpoints for DNA sequencing. Gene 28:351–359.

(8) Sanger, F., Nicklen, S. and Coulson, A. R. (1977) DNA sequencing with chain terminating inhibitors. Proc. Natl. Acad. Sci. USA 74:5463–5466.

(9) Devereux, J., Haeberli, P. and Smithies, O. (1984) A comprehensive set of sequence analysis programs for the VAX. Nucleic Acids Res. 12:387–395.

(10) Gaboriaud, C., Bissery, V., Benchetrit, T. and Mornon, J. P. (1987) Hydrophobic cluster analysis: an efficient way to compare and analyse amino acid sequences. FEBS Lett. 224:149–155.

(11) Lemesle-Varloot, L., Henrissat, B., Gaboriaud, C., Bissery, V., Morgat, A. and Mornon, J. P. (1990) Hydrophobic cluster analysis: procedures to derive structural and functional information from 2-D-representation of protein sequences. Biochimie 72:555–574.

(12) Lee, C., Bagdasarian, M., Meng, M. and Zeikus, J. G. (1990) Catalytic mechanism of xylose (glucose) isomerase from *Clostridium thermosulfurigenes.* J. Biol. Chem. 265:19082–19090.

(13) Lee, C. and Zeikus, J. G. (1991) Purification and characterization of thermostable glucose isomerase from *Clostridium thermosulfurigenes* and *Thermoanaerobacter* strain B6A. Biochem. J. 274:565–571.

(14) Bradford, M. M. (1976) A rapid and sensitive method for quantitation of microgram quantities of protein utilizing the principle of protein-dye binding. Analytical Biochemistry 72:248–254.

(15) Dische, Z. and Borenfreund, E. (1951) A new spectrophotometric method for the detection and determination of keto sugars and trioses. J. Biol. Chem. 192:583–587.

(16) Dawson, R. M., Elliott, D. C., Elliott, W. H. and Jones, K. M. (eds.) Data for biochemical research (1969) Oxford University Press, Ely House, London, U.K.

(17) Amore, R. and Hollenberg, C. P. (1989) Xylose isomerase from *Actinoplanes missouriensis*: primary structure of the gene and the protein. Nucleic Acids Res. 17:7515.

(18) Saari, G. C., Kumar, A. A., Kawasaki, G. H., Insley, M. Y. and O'Hara, J. (1987) Sequence of the Ampullariella sp. strain 3876 gene coding for xylose isomerase. J. Bacteriol. 169:612–618.

(19) Wong, H. C., Ting, Y., Reichert F., My Ambo, K., Watt, K. W. K., Toy, P. L. and Drummond, R. J. (1991) Genetic organization and regulation of the xylose degradation genes in *Streptomyces rubiginosus.* J. Bacteriol. 173:6849–6858.

(20) Drocourt, D., Bejar, S., Calmels, T., Reynes, J. P. and Tiraby, G. (1988) Nucleotide sequence of the xylose isomerase gene from *Streptomyces violaceoniger*. Nucleic Acids Res. 19:9337.

(21) Wilhelm, M. and Hollenberg, C. P. (1985) Nucleotide sequence of the *Bacillus subtilis* xylose isomerase gene: extensive homology between the Bacillus and *Escherichia coli* enzymes.

(22) Bor, Y. -C., Moraes, C., Lee, S. -P., Crosby, W. L., Sinskey, A. J. and Batt, C. A. (1992) Cloning and sequencing the *Lactobacillus brevis* gene encoding xylose isomerase. Gene 114:127–131.

(23) Lokman, B.C., van Santen, P., Verdoes, J. C., Krüse, J., Leer, R. J., Posno, M. and Pouwels, P. H. (1991) Organization and characterization of three genes involved in D-xylose catabolism in *Lactobacillus pentosus*. Mol. Gen. Genet. 230:161–169.

(24) Sizemore, C., Buchner, E., Rygus, T., Witke, C., Götz, F. and Hillen, W. (1991) Organization, promoter analysis and transcriptional regulation of the *Staphylococcus xylosus* xylose utilization operon. Mol. Gen. Genet. 227:377–384.

(25) Schellenberg, G. D., Sarthy, A., Larson, A. E., Backer, M. P., Crabb, J. W., Lidstrom, M., Hall, B. D. and Furlong, C. E. (1983) Xylose isomerase from *Escherichia coli*. Characterization of the protein and the structural gene. J. Biol. Chem. 259:6826–6832.

(26) Achenbach-Richter, L., Gupta, R., Stetter, K.-O and Woese, C. R. (1987) Were the original eubacteria thermophiles? System. Appl. Microbiol. 9:34–39.

(27) Lao, D. and Dennis, P. P. (1992) The organization and expression of essential transcription translation components genes in the extremely thermophilic eubacterium *Thermotoga maritima*. JBC 267:22787–22797.

(28) Fürste, J. P., Pansegrau, W., Frank, R., Blöcker, H., Scholz, P., Bagdasarian, M. and Lanka, E. (1986) Molecular cloning of the plasmid RP4 primase region in a multi-host-range tacP expression vector. Gene 48:119–131.

We claim:

1. An isolated hyperthermostable xylose isomerase gene comprising a DNA obtained from chromosomal DNA from *Thermotoga neapolitana* DSM 5068, said obtained DNA encoding a hyperthermostable xylose isomerase and having the nucleotide sequence of SEQ ID NO:2.

2. A recombinant vector containing the DNA sequence of SEQ ID NO:2.

3. A method of producing a hyperthermostable xylose isomerase which comprises isolating the xylose isomerase gene of claim 1 from *T. neapolitana*, constructing a hybrid plasmid, inserting the hybrid plasmid into a host microorganism that expresses the enzyme and then purifying the enzyme by heating it to a temperature which denatures most of the contaminating proteins.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2522 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
GTCGACGCAA  AGGTCGTGAC  GGGTGGAAAC  ATAAACGTTC  AGCTGGGAAC  TGTGTCCTCG        60

GCTGCTGTTG  AAGGAACATA  CGTTATCGAA  GTTGGACAAT  TCTCTGGAAC  GGTCACATCC       120

GAGCTTGATG  TCAAGATCCG  CCGTTGTCCT  CAGCACCCCT  TCCGTACACC  CTGTCATCCT       180

TCACAACGGG  GATGAAGGGA  TCCGTTTCCC  ACAGCGAAAG  ATCCCTGGT   GGAACGGTGT       240

CTATGTGTGT  CACTATCCAC  AATGTTTTGC  TTCTGTCCCT  GCCGGGAATG  ATTGCAAGCA       300

GATTCGACCT  CCAAATTCCG  TTCTGGTCTT  TTGTGTCATG  ACGCTCAACA  GTGTATCCCA       360

TCTTTTTGAG  AAGTTCCTCC  AGCCAGTCGG  CCTTCTCTTT  CTCTCCAGGT  CCACCGAAGA       420

CTGGATTCAC  CGAATTGATC  GATATGAACC  TTTTCAGCGA  ATCTACCATT  TCGTCTTTCA       480

ATTCTTCTAT  CTTTCTTGTT  ATCTCCATCT  GAAACACCTC  CCAAGTACAA  GTATATCTCT       540

CCAAAAAAT   ATTTGAAATG  ACCCCAGGGA  ATTTTATATA  ATTGATTGAT  AGAAAAAATT       600

TAGGGAGGTG  TTCACATGGC  TGAATTCTTT  CCAGAAATCC  CGAAAGTGCA  GTTCGAAGGC       660

AAAGAAAGCA  CAAATCCACT  TGCGTTCAAG  TTCTACGATC  CAGAAGAGAT  CATCGACGGC       720

AAACCCCTCA  AGGACCATCT  GAAGTTCTCC  GTTGCCTTCT  GGCACACCTT  CGTGAACGAG       780

GGAAGGGATC  CCTTCGGAGA  CCCAACGGCC  GATCGTCCCT  GGAACAGGTA  CACCGATCCC       840

ATGGACAAGG  CTTTTGCAAG  GGTGGACGCC  CTTTTTGAAT  TCTGCGAAAA  ACTCAACATC       900

GAGTACTTCT  GCTTCCACGA  CAGAGACATC  GCTCCCGAGG  GAAAAACGCT  GAGGGAGACA       960

AACAAAATTT  TGGACAAAGT  AGTGGAGAGA  ATCAAAGAGA  GAATGAAAGA  CAGCAACGTG      1020

AAGCTCCTCT  GGGGTACTGC  AAACCTCTTT  TCCCACCCAA  GGTACATGCA  TGGTGCAGCG      1080
```

-continued

| | | | | | |
|---|---|---|---|---|---|
| ACAACCTGCA | GTGCTGATGT | TTTTGCGTAC | GCGGCCGCCC | AGGTGAAAAA | AGCCCTTGAG | 1140 |
| ATCACCAAAG | AACTTGGAGG | AGAAGGGTAC | GTCTTCTGGG | GTGGAAGAGA | AGGATACGAA | 1200 |
| ACACTCCTCA | ACACGGACCT | TGGATTCGAA | CTTGAAAACC | TCGCCCGCTT | CCTCAGAATG | 1260 |
| GCTGTGGATT | ATGCAAAAAG | GATCGGTTTC | ACCGGACAGT | TCCTCATCGA | ACCAAAACCG | 1320 |
| AAAGAACCCA | CCAAACACCA | GTACGACTTC | GACGTTGCAA | CCGCCTATGC | CTTCCTGAAG | 1380 |
| AGCCACGGTC | TCGATGAATA | CTTCAAATTC | AACATCGAGG | CAAACCACGC | CACACTCGCC | 1440 |
| GGTCACACCT | TCCAGCACGA | ACTGAGAATG | GCAAGGATCC | TTGGAAAACT | CGGAAGCATC | 1500 |
| GATGCAAACC | AGGGAGACCT | TCTTCTTGGA | TGGGACACCG | ATCAGTTCCC | AACAAACGTC | 1560 |
| TACGATACAA | CCCTTGCAAT | GTACGAAGTG | ATAAAAGCGG | GAGGCTTCAC | AAAAGGTGGG | 1620 |
| CTCAACTTCG | ATGCGAAGGT | GAGGAGGGCT | TCTTACAAAG | TGGAGGACCT | CTTCATAGGG | 1680 |
| CACATAGCGG | GAATGGACAC | CTTTGCACTC | GGTTTCAAGG | TGGCATACAA | ACTCGTGAAG | 1740 |
| GATGGTGTTC | TGGACAAATT | CATCGAAGAA | AAGTACAGAA | GTTTCAGGGA | GGGCATTGGA | 1800 |
| AGGGACATCG | TCGAAGGTAA | AGTGGATTTT | GAAAAACTTG | AAGAGTATAT | AATAGACAAA | 1860 |
| GAAACGATAG | AACTTCCATC | TGGAAAGCAA | GAATACCTGG | AAAGCCTCAT | CAACAGTTAC | 1920 |
| ATAGTGAAGA | CCATTCTGGA | ACTGAGGTGA | AACAGAGTGT | GAAGTTCTTG | AATCTTCGAA | 1980 |
| GATTACTTCT | TCTGGCACTG | ATTGCGGCTG | GAATCTCAGT | GATCATAGTC | GTATCCAACC | 2040 |
| GGGAAAACAG | GGTGAAATTT | CCAGAAGGAG | AGATTGTGAT | AACTGACGGA | GAAAGATCTC | 2100 |
| TGAAACTTCG | TGTCGAGATA | GCGAACACTC | CTTTTTTTCG | TTCGATCGGT | CTGATGTACA | 2160 |
| GAAAGAGCAT | CCCGGATGAC | TTCGGGATGC | TCTTTGTTTT | TGAAGAAGAT | ACAAGAAGCG | 2220 |
| GCTTCTGGAT | GAAGAACACC | TACGTTCCCC | TCGAAATCGC | CTTCATAGAC | AGAAACGGCA | 2280 |
| TCGTATTTTC | CATTCAGGAG | ATGGAGCCAT | GCGAAAAGA | ACCTGCAAG | GTTACTACG | 2340 |
| CACCAAAGCC | GTTCAGATAC | GCTCTTGAAG | TGAAAAGAGG | TTTTTTCGAA | AGGCATGGAT | 2400 |
| TTGGAGTGGG | AAGCCGTGTC | CTGATAGAAA | AGTAGCGGTA | CTTTCAAACA | AAAACGTATG | 2460 |
| GAATCTTCAT | CTTCTTTGCC | TCGTACATTC | TCGAGTCAGC | CATCTTCAGA | AGTTCTTCTA | 2520 |
| GA | | | | | | 2522 |

( 2 ) INFORMATION FOR SEQ ID NO:2:

( i ) SEQUENCE CHARACTERISTICS:
        ( A ) LENGTH: 444 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Met Ala Glu Phe Phe Pro Glu Ile Pro Lys Val Gln Phe Glu Gly Lys
 1               5                  10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95
```

```
Tyr Phe Cys Phe His Asp Arg Asp Ile Ala Pro Glu Gly Lys Thr Leu
            100             105             110

Arg Glu Thr Asn Lys Ile Leu Asp Lys Val Val Glu Arg Ile Lys Glu
        115             120             125

Arg Met Lys Asp Ser Asn Val Lys Leu Leu Trp Gly Thr Ala Asn Leu
    130             135             140

Phe Ser His Pro Arg Tyr Met His Gly Ala Ala Thr Thr Cys Ser Ala
145             150                 155             160

Asp Val Phe Ala Tyr Ala Ala Ala Gln Val Lys Lys Ala Leu Glu Ile
            165             170             175

Thr Lys Glu Leu Gly Gly Glu Gly Tyr Val Phe Trp Gly Gly Arg Glu
        180             185             190

Gly Tyr Glu Thr Leu Leu Asn Thr Asp Leu Gly Phe Glu Leu Glu Asn
        195             200             205

Leu Ala Arg Phe Leu Arg Met Ala Val Asp Tyr Ala Lys Arg Ile Gly
    210             215             220

Phe Thr Gly Gln Phe Leu Ile Glu Pro Lys Pro Lys Glu Pro Thr Lys
225             230             235             240

His Gln Tyr Asp Phe Asp Val Ala Thr Ala Tyr Ala Phe Leu Lys Ser
            245             250             255

His Gly Leu Asp Glu Tyr Phe Lys Phe Asn Ile Glu Ala Asn His Ala
        260             265             270

Thr Leu Ala Gly His Thr Phe Gln His Glu Leu Arg Met Ala Arg Ile
        275             280             285

Leu Gly Lys Leu Gly Ser Ile Asp Ala Asn Gln Gly Asp Leu Leu Leu
    290             295             300

Gly Trp Asp Thr Asp Gln Phe Pro Thr Asn Val Tyr Asp Thr Thr Leu
305             310             315             320

Ala Met Tyr Glu Val Ile Lys Ala Gly Gly Phe Thr Lys Gly Gly Leu
            325             330             335

Asn Phe Asp Ala Lys Val Arg Arg Ala Ser Tyr Lys Val Glu Asp Leu
        340             345             350

Phe Ile Gly His Ile Ala Gly Met Asp Thr Phe Ala Leu Gly Phe Lys
    355             360             365

Val Ala Tyr Lys Leu Val Lys Asp Gly Val Leu Asp Lys Phe Ile Glu
    370             375             380

Glu Lys Tyr Arg Ser Phe Arg Glu Gly Ile Gly Arg Asp Ile Val Glu
385             390             395             400

Gly Lys Val Asp Phe Glu Lys Leu Glu Glu Tyr Ile Ile Asp Lys Glu
            405             410             415

Thr Ile Glu Leu Pro Ser Gly Lys Gln Glu Tyr Leu Glu Ser Leu Ile
        420             425             430

Asn Ser Tyr Ile Val Lys Thr Ile Leu Glu Leu Arg
        435             440
```